USOO5405872A

United States Patent [19]
McDermed et al.

[11] Patent Number: 5,405,872
[45] Date of Patent: Apr. 11, 1995

[54] ANTI-HYPERTENSIVE TETRALINS

[75] Inventors: John D. McDermed, Chapel Hill; Kevin P. Hurley, Durham, both of N.C.; Vincent H. Chang, Lake Forest, Ill.; Anjaneyulu S. Tadepalli, Durham, N.C.

[73] Assignee: Burroughs Wellcome Co., Research Triangle Park, N.C.

[21] Appl. No.: 30,018

[22] PCT Filed: Sep. 19, 1991

[86] PCT No.: PCT/GB91/01602
§ 371 Date: Mar. 22, 1993
§ 102(e) Date: Mar. 22, 1993

[87] PCT Pub. No.: WO92/05143
PCT Pub. Date: Apr. 2, 1992

[30] Foreign Application Priority Data

Sep. 22, 1990 [GB] United Kingdom ............... 9020695

[51] Int. Cl.⁶ .......................................... A61K 31/18
[52] U.S. Cl. .................................... 514/605; 564/99
[58] Field of Search ............... 514/603, 605; 564/86, 564/99

[56] References Cited

U.S. PATENT DOCUMENTS 4,379,166  4/1983  Neustadt et al. ............... 424/324
5,102,914  4/1992  McDermed et al. ............. 514/605

FOREIGN PATENT DOCUMENTS 0338793  10/1989  European Pat. Off. .
1249261  10/1971  United Kingdom .

OTHER PUBLICATIONS

Chemical Abstract 102(19):160032 and Structure 1984.
Chemical Abstract 98(17):137214 and Structures 1983.
Glynn et al., "Halogen Analogues of Adrenaline and Ephedrine", Quarterly Journal of Pharmacy and Pharmacology, 5, 480–495 (1932).
Fieser et al., "1′-Methyl- and 1′,10-Dimethyl-1,2-benzanthracene", J. Am. Chem. Soc., 60, 170–176 (1938).
Veterans Administration Cooperative Study Group on Antihypertensive Agents, "Effects of Treatment on Morbidity in Hypertension, Results in Patients with Diastolic Blood Pressure Averaging 115 through 129 mm Hg", JAMA, 202(11), 116–122 (1967).
Veterans Administration Cooperative Study Group on Antihypertensive Agents, "Effects of Treatment on Morbidity in Hypertension, II. Results in Patients With Diastolic Blood Pressure Averaging 90 through 114 mm Hg", JAMA, 213(7), 1143–1152 (1970).
Leclerc et al., "Synthesis and Structure–Activity Relationships among α-Adrenergic Receptor Agonists of the Phenylethanolamine Type", J. Med. Chem., 23(7), 738–744 (1980).
Woods, "Hypertension", Current Therapy, Editor: Conn, H. F., 219–223 (1981).
Takashi et al., "Studies on Benzenesulfonamide Derivatives with α- and β-Adrenergic Antagonistic and Antihypertensive Activities", Chem. Pharm. Bull., 30(11), 4092–4101 (1982).
Schlicker, E. et al., "Increased Affinity and Preference of Halogenated Derivatives of BE 2254 for $\alpha_1$-Adrenoceptors Demonstrated by Functional and Binding Experiments", Journal of Cardiovascular Pharmacology, 6, 1238–1244 (1984).

Primary Examiner—José G. Dees
Assistant Examiner—Samuel Barts
Attorney, Agent, or Firm—Hannah O. Green; Fran S. Wasserman

[57] ABSTRACT

This invention relates to tetralin derivatives useful in medicine for the treatment of hypertension, to the synthesis of the compounds, to the pharmaceutical formulations containing the compounds and the use of the compounds in medical practice.

4 Claims, No Drawings

ANTI-HYPERTENSIVE TETRALINS

FIELD OF THE INVENTION

This invention relates to tetralin derivatives useful in medicine for the treatment of hypertension, to the synthesis of the compounds, to pharmaceutical formulations containing the compounds and the use of the compounds in medical practice.

BACKGROUND INFORMATION

Hypertension may be defined as a condition of sustained elevated arterial blood pressure, i.e., a diastolic pressure in excess of 90 mm Hg. In the majority of cases, the patients are affected by essential hypertension, which by definition means that the underlying etiologic mechanism(s) is unknown. Regardless of the mechanism, a sustained elevation of blood pressure for a period of time has been shown to result in significant cardiovascular damage throughout the body, e.g., congestive heart failure, coronary artery disease, stroke and progressive renal failure [Veterans Administration Cooperative Study Group on Antihypertensive Agents: Effects of Treatment on Morbidity in Hypertension. Results in patients with diastolic blood pressures averaging 115 through 129 mm Hg, J.A.M.A., (1967), 202, 1028 and Veterans Administration Cooperative Study Group on Antihypertensive Agents: Effects of Treatment on Morbidity in Hypertension II. Results in patients with diastolic blood pressures averaging 90 through 114 mm Hg, J.A.M.A., (1970), 213, 1143].

The benefits of drug therapy to reduce and control blood pressure have been established [Woods, J. W., Current Therapy, ed. Conn, H. F., pp. 219–220, 1981]. Since the specific etiology is not usually known, an empirical approach to the treatment of hypertensive patients is taken. Often, the choice of treatment is based on the severity of the disease and the patient's response and compliance to initial therapy. The goal of the treatment is to reduce elevated blood pressure and maintain pressure at or near normal levels. An antihypertensive agent should be Orally active and have a sufficiently prolonged duration of action to normalize hemodynamic derangements in humans.

European Patent Specification No. 338793 describes certain tetralin sulfonanilides for use in the treatment of prophylaxis of hypertension.

SUMMARY OF THE INVENTION

The compounds of the present invention may be characterized by formula (I)

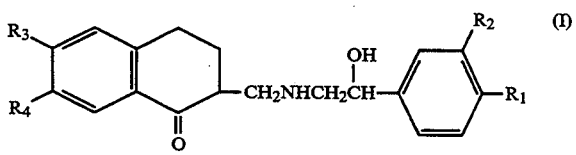

wherein $R_1$ is hydrogen, hydroxy, $C_{1-4}$ alkyl, halo (e.g., chloro), carbamoyl, aminosulfonyl, $C_{1-4}$ alkylsulfonylamino or $C_{1-4}$ alkyl($C_{1-4}$ alkylsulfonyl)amino; $R_2$ is hydrogen, hydroxy, halo carbamoyl(e.g., chloro) $C_{1-4}$ alkoxycarbonyl, aminosulfonyl or $C_{1-4}$ alkylsulfonylamino; $R_3$ is hydrogen, hydroxy or $C_{1-4}$ alkoxy; $R_4$ is hydrogen, $C_{1-4}$ alkoxy, halo (e.g., chloro or bromo) or nitro and pharmaceutically acceptable salts thereof provided that $R_1$ and $R_2$ are not both hydrogen and that when $R_1$ is methylsulfonylamino and $R_4$ is hydrogen, $R_3$ is not hydrogen or $C_{1-4}$ alkoxy. The invention also includes all enantiomeric and diastereoisomeric forms of the compounds of formula (I), either individually or admixed in any proportions and pharmaceutically acceptable salts thereof.

The compounds of the invention have been found to have advantageous potent antihypertensive properties and are therefore useful in controlling elevated blood pressure in mammals such as humans.

DETAILED DESCRIPTION OF THE INVENTION

Compounds of formula (I) and their salts may be synthesized by methods known in the art for the synthesis of compounds having analogous structures. In particular, compounds of formula (I) and their salts may be prepared by any of the following processes which constitute further aspects of the present invention. For the preparation of compounds of formula (I), a compound of formula (II)

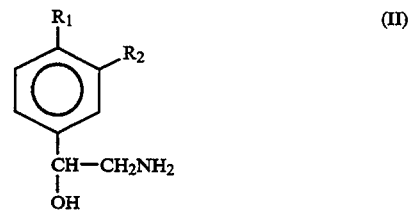

wherein $R_1$ and $R_2$ are as hereinbefore defined, may be reacted with a compound of formula (IV)

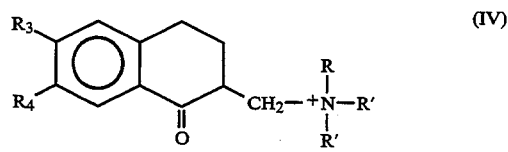

wherein $R_3$ and $R_4$ are as hereinbefore defined and R is lower alkyl, and R' is lower alkyl or R'R' is an alicyclic ring, or with a compound of formula (III)

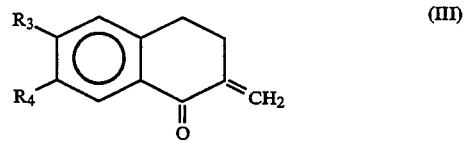

wherein $R_3$ and $R_4$ are as hereinbefore defined.

Thus compounds of formula (I) as above described are Mannich bases and may be prepared by standard methods well known to chemists. With reference to Scheme I, one method for preparing such compounds comprises reacting a primary amine of formula (II) with a quaternary ammonium salt of formula (IV) or with a functional equivalent thereof such as the corresponding exo-methylene ketone (III).

Compounds of formula (IV) wherein $R_3$, $R_4$, R and R' are as hereinbefore defined may be synthesized by reacting an amine of formula (V) with a suitable alkylating agent RL, where L is a leaving group such as halide, for example methyl iodide.

The compounds of formula (V) are Mannich bases and may be prepared by standard methods, for example, by reacting a ketone of formula (VI) with formaldehyde, or a functional equivalent thereof such as paraformaldehyde, and a secondary amine of formula $HN(R')_2$ or a salt thereof, by heating the mixture in a solvent, preferably a lower alcohol, in the presence of an acid. Alternatively, primary amines of formula (II) may be used in lieu of a secondary amine in the Mannich reaction to yield compounds of formula (I) directly. However, those skilled in the art will realize that primary amines generally give poor yields in such reactions.

Compounds of formula (II), (III), and (VI) are either commercially available or may be prepared by general methods available from the chemical literature.

In particular, compounds of formula (II) may be prepared from numerous possible starting materials via a variety of different routes well documented in the literature and known to chemists. Several of the more common routes are outlined in Scheme II. In particular, one preferred method of preparing compounds of formula (II) wherein $R_1$ and/or $R_2$ are not halogen and X is dibenzyl or a functional equivalent thereof, consists of the reduction and hydrogenolysis of compounds of formula (VII) in a single step using three molecular equivalents of hydrogen in the presence of a metal catalyst such as palladium or platinum. The catalyst may be free or deposited on any suitable support such as carbon. Alternatively, the compounds of formula (II) wherein $R_1$ and/or $R_2$ are not halogen may be prepared by a two step reduction of compounds of formula (VII). The first step (reduction of the carbonyl group) may be accomplished with a wide variety of reducing agents well known to those skilled in the art, such as complex hydrides (e.g., $NaBH_4$ or $LiAlH_4$) or borane type reagents (e.g., diborane), to give a compound of formula (X) which is then hydrogenolyzed using two molecular equivalents of hydrogen to give the compounds of formula (II).

Compounds of formula (VII) may be prepared by reacting a bromoketone of formula (IX) with ammonia or, preferably, a functional equivalent thereof (HNX), such as dibenzylamine or a functional equivalent thereof, hexamethylenetetramine (HMTA), or phthalimide. Compounds of formula (IX) are commercially available or may be prepared by the general methods reported in the chemical literature.

Compounds of formula (X) may be prepared by reacting an epoxide of formula (XII) with a functional equivalent of ammonia (HNX), such as dibenzylamine, hexamethylenetetramine, or phthalimide. Hydrogenolysis (when NX is dibenzylamine), acidic hydrolysis (when NX is HMTA), or hydrazinolysis (when NX is phthalimide) of compounds of formula (X) will yield compounds of formula (II). Reaction of compounds of formula (XII) with ammonia itself gives compounds of formula (II) directly. Compounds of formula (XII) are commercially available or may be prepared by the general methods reported in the chemical literature.

In the case of compounds of formula (II) wherein $R_1$ and/or $R_2$ are halogen, the above described routes are unsuitable. One of the general methods which may be employed to prepare such compounds is outlined in Scheme II. In particular, reacting a bromoketone of formula (IX) with ammonia or, preferably, a functional equivalent thereof (HNX), such as hexamethylenetetramine, or phthalimide, results in a compound of formula (XI). Acidic hydrolysis of the compound of formula (XI) when NX is HMTA, or hydrazinolysis of compounds of formula (XI) when NX is phthalimide, produce the aminoketone (VIII) which may be reduced using a complex hydride or a borane reagent to give the compound of formula (II). As indicated, compounds of formula (IX) are commercially available or may be prepared by the general methods reported in the chemical literature. This general scheme is also acceptable when $R_1$ and $R_2$ are not halogen.

Alternatively, the compounds of formula (II) wherein $R_1$ and/or $R_2$ are halogen may be prepared according to Scheme 3 by reacting the commercially available compounds of formula (XIII) with $NaHSO_3$ and NaCN to give the cyanohydrin (XIV) which is reduced by $LiAlH_4$ to the compounds of formula (II).

It will be appreciated by chemists that compounds of formula (II) contain an asymmetric carbon atom and that the use of achiral reducing agents in the preparation of these compounds from a compound of formula (VII) or (VIII) will produce racemic products, whereas the use of chiral reducing agents in analogous reactions may produce products enriched in one of the two possible enantiomers. Separately reacting the enantiomers of (II) with compounds of formula (III) or (IV) will produce optically active products composed of two diastereoisomers. Fractional crystallization of the diastereoisomers or chromatography of the mixture may result in products of formula (I) which are enriched in one of the possible diastereoisomers.

Scheme I

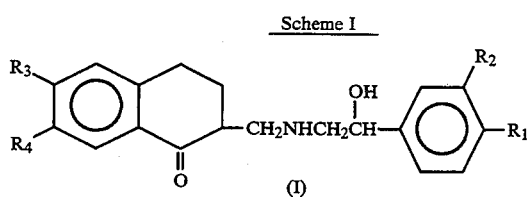

(I)

Scheme I
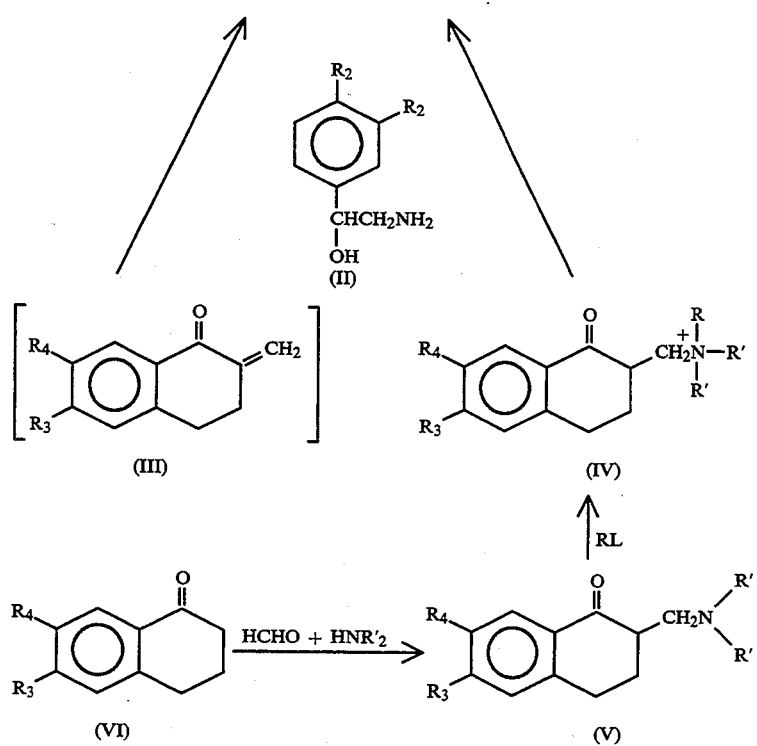
Scheme II
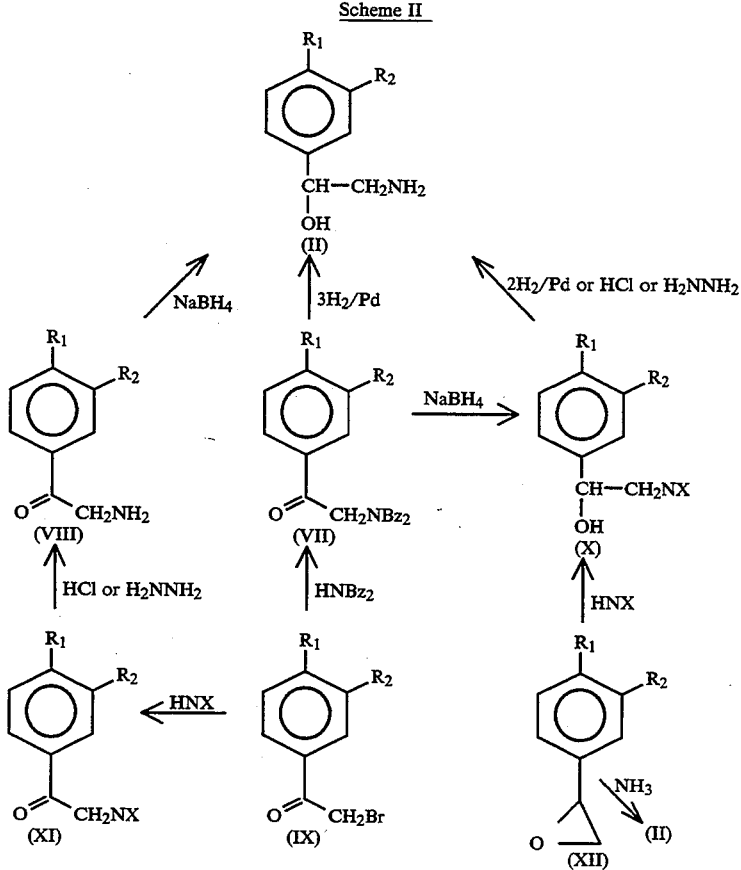
where NX is phthalimide or HMTA

Scheme III

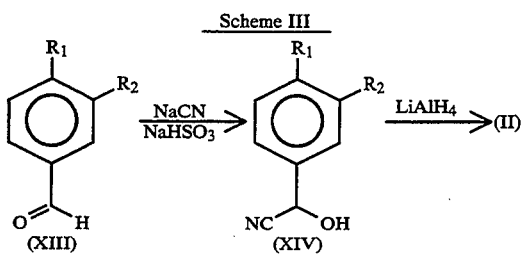

Compounds of formula (I) which were found to be active as antihypertensive agents are:

| Compound | Example No. | $R_1$ | $R_2$ | $R_3$ | $R_4$ |
|---|---|---|---|---|---|
| XV* | 1 | $CH_3$ | $SO_2NH_2$ | H | H |
| XVI* | 2 | $CH_3$ | $SO_2NH_2$ | $OCH_3$ | H |
| XVII* | 3 | $CH_3$ | $SO_2NH_2$ | H | H |
| XVIII* | 4 | $CH_3$ | $SO_2NH_2$ | H | H |
| XIX* | 5 | $CH_3$ | $SO_2NH_2$ | $OCH_3$ | H |
| XX* | 6 | $CH_3$ | $SO_2NH_2$ | $OCH_3$ | H |
| XXI | 7 | $CH_3$ | $SO_2NH_2$ | $OCH_3$ | $OCH_3$ |
| XXII | 8 | H | OH | H | H |
| XXIII | 9 | OH | H | H | H |
| XXIV | 10 | OH | $CO_2CH_3$ | H | H |
| XXV | 11 | Cl | H | H | H |
| XXVI | 12 | Cl | $NHSO_2CH_3$ | H | H |
| XXVII | 13 | Cl | H | $OCH_3$ | H |
| XXVIII | 14 | Cl | $NHSO_2CH_3$ | H | Cl |
| XXIX | 15 | $NHSO_2CH_3$ | H | H | Cl |
| XXX | 16 | Cl | Cl | H | H |
| XXXI | 17 | OH | $CONH_2$ | H | H |
| XXXII | 18 | OH | $CONH_2$ | $OCH_3$ | H |
| XXXIV | 20 | $NHSO_2C_2H_5$ | H | H | H |
| XXXV | 21 | $N(CH_3)SO_2CH_3$ | H | H | H |
| XXXVI | 22 | $N(CH_3)SO_2CH_3$ | H | $OCH_3$ | H |
| XXXVII | 23 | $NHSO_2CH_3$ | H | H | Br |
| XXXVIII | 24 | $NHSO_2CH_3$ | H | H | $OCH_3$ |
| XXXIX | 25 | $NHSO_2CH_3$ | H | $OCH_3$ | $OCH_3$ |
| XL | 26 | $NHSO_2CH_3$ | H | H | $NO_2$ |
| XLI | 27 | $NHSO_2CH_3$ | H | OH | H |

*Optical Isomers

The compounds of formula (I) may be used in the treatment of hypertension in mammals, including humans, when administered in therapeutically effective amounts.

According to a further aspect of the present invention, therefore, there is provided a method for the treatment of hypertension in a mammal which comprises administering to said mammal a therapeutically effective amount of a compound of formula (I) or a pharmaceutically acceptable salt thereof.

According to further aspects, the invention also provides a compound of formula (I), or a pharmaceutically acceptable salt thereof, for use in therapy, for example, the treatment of hypertension, and for the use of a compound of formula (I), or a pharmaceutically acceptable salt thereof, in the manufacture of a therapeutic agent for the treatment of hypertension.

The effective antihypertensive amount of active compound required for use in the above conditions will vary both with the route of administration, the condition under treatment and the mammal undergoing treatment, and is ultimately at the discretion of the physician. A suitable oral dose of the active compound for a mammal is in the range of from about 1 to about 50 mg per kilogram body weight per day; preferably from about 2 to about 20 mg/kg. For example, a typical dose for a human recipient of the active compound is about 10 mg/kg body weight per day. The desired dose is preferably presented as from one to three sub-doses administered at appropriate intervals throughout the day. Where three sub-doses of compounds of formula (I) are employed, each will preferably lie in the range of from about 2 to about 7 mg/kg body weight; for example, a typical sub-dose of the active compound for a human recipient is about 250 mg.

A suitable parenteral dose of the active compound for a mammal is in the range of from about 0.05 to about 5.0 mg per kilogram body weight per day, preferably from about 0.1 to about 4.0 mg/kg.

While it is possible for the active compound to be administered alone as the raw chemical, it is preferable to present the active compound as a pharmaceutical formulation. Formulations of the present invention, both for veterinary and for human medical use, comprise the active compound together with one or more pharmaceutically acceptable carriers therefor and optionally any other therapeutic ingredients. The carrier(s) must be pharmaceutically acceptable in the sense of being compatible with the other ingredients of the formulation and not deleterious to the recipient.

The formulations include those suitable for oral, transdermal, rectal or parenteral (including subcutaneous, intramuscular and intravenous) administration. Formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier, or both, and then, if necessary, shaping the product into the desired formulation.

Formulations of the present invention suitable for oral administration may be presented as discrete units such as capsules, cachets, tablets or lozenges, each containing a predetermined amount of the active compound; as a powder or granules; or as a suspension in an aqueous liquid or non-aqueous liquid such as a syrup, an elixir, an emulsion or a draught.

A tablet may be made by compression or molding, optionally with one or more accessory ingredients. Compressed tablets may be prepared by compressing in a suitable machine, the active compound being in a free-flowing form such as a powder or granules, optionally mixed with a binder, disintegrants, lubricant, inert diluent, or surface active/dispersing agent. Molded tablets, comprising a mixture of the powdered active compound with any suitable carrier, may be made by molding in a suitable machine. The tablets may optionally be coated or scored and may be formulated so as to provide slow or controlled release of the active ingredient therein. The tablets may optionally be provided with an enteric coating to release in parts of the gut other than the stomach.

A syrup may be made by adding the active compound to a concentrated, aqueous solution of a sugar; for example, sucrose, to which may also be added any accessory ingredient(s). Such accessory ingredient(s) may include flavorings, an agent to retard crystallization of the sugar or an agent to increase the solubility of any other ingredient, such as a polyhydric alcohol, for example, glycerol or sorbitol, and suitable preservatives.

Formulations suitable for parenteral administration conveniently comprise a sterile aqueous preparation of the active compound Which is preferably isotonic with the blood of the recipient.

In addition to the aforementioned ingredients, the formulations of this invention may further include one or more accessory ingredient(s) selected from diluents, buffers, flavoring agents, binders, disintegrants, surface active agents, thickeners, lubricants, preservatives (including antioxidants) and the like.

When used in medicine, the salts of the compound of formula (I) should be pharmaceutically acceptable acid addition salts, but pharmaceutically unacceptable salts may conveniently be used to prepare the base or pharmaceutically acceptable salts of the base, and are not excluded from the scope of this invention. Suitable pharmaceutically acceptable salts include, but are not limited to, those prepared from the following acids: hydrochloric, hydrobromic, hydroiodic, sulfuric, nitric, phosphoric, maleic, salicylic, p-toluenesulfonic, tartaric, citric, acetic, methanesulfonic, formic, succinic, naphthalene-2-sulfonic, isethionic, lactobionic and benzenesulfonic.

EXAMPLES

The following Examples are provided by way of illustration of the present invention and should in no way be construed as a limitation thereof.

Example 1. Preparation of 5-(1-Hydroxy-2-(((1,2,3,4-tetrahydro-1-oxo-2-naphthyl)methyl)amino)ethyl)-2-methylbenzenesulfonamide Hydrochloride (XV.HCl)

Compound XLIII (3.5 g), compound XLIV (2.7 g) and triethylamine (1.8 mL) were combined in acetonitrile (40 mL) and stirred at ambient temperature for 18 hours. Solids were removed by filtration and were determined to be predominantly unreacted XLIV. The filtrate was evaporated to dryness and the residue was dissolved in EtOAc, which was washed with saturated $NaHCO_3$ solution and water, and was then acidified with 1.5 mL concentrated HCl in 10 mL MeOH. The solution was evaporated to dryness and the solid residue was recrystallized from 95% acetonitrile/5% water which produced a batch of crude product (0.85 g). The filtrate from this solid was treated with hot EtOAc until a solid precipitated which was crystallized from EtOH/EtOAc to give a second batch of crude product (0.19 g). The two batches of crude product were combined and recrystallized twice from MeOH and EtOAc. This yielded 0.69 g of compound XV.HCl, m.p. 190°–192° C. (dec) whose NMR and mass spectrum were consistent with the structure, and whose elemental analyses for C, H, and N were within 0.1% of the calculated values.

A. Preparation of N-(1,2,3,4-Tetrahydro-1-oxo-2,naphthyl)methyl-N,N,N-trimethylammonium Iodide XLIII)

Paraformaldehyde (43 g), 1-oxo-1,2,3,4-tetrahydronaphthalene (Aldrich Chemical Co., Milwaukee, Wis. 53233) (100 g), dimethylamine hydrochloride (61.5 g) and concentrated HCl (11.4 mL) were combined in EtOH (380 mL) and heated at reflux for 18 hours. Upon dilution with acetone (3000 mL) and cooling to 4° C., a precipitate appeared, which was filtered off and partitioned between EtOAc and excess aqueous $NaHCO_3$. The EtOAc layer was dried ($MgSO_4$) and evaporated, leaving 90 g of oil. This oil was combined with methyl iodide (54 g) in acetone (100 mL) and stirred at ambient temperature for 1 hour. This resulted in precipitation of compound XLIII (96 g) as a white solid, m.p. 199°–200° C., which was used without further purification.

B. Preparation of 5-((1-Hydroxy-2-amino)ethyl)-2-methylbenzenesulfonamide Hydrochloride (XLIV.HCl)

Compound XLV.HCl (25.0 g) and 20% Pd/C (0.75 g) were combined in MeOH (250 mL) and heated at 38° C. for 20 hours in a Parr hydrogenator under an average hydrogen pressure of 3 atmospheres. The catalyst was filtered off and fresh 20% Pd/C (0.75 g) was added to the filtrate. The mixture was returned to the Parr hydrogenator and heated at 35° C. under an average pressure of 3 atmospheres hydrogen for an additional 20 hr. The catalyst was filtered off and the filtrate was evaporated to dryness. The residue was dissolved in hot 95% EtOH (100 mL) from which an undesired component (the monobenzylamine of XLIV.HCl) crystallized. The solid was filtered off and the filtrate was evaporated to dryness. The residue was recrystallized once from MeOH/EtOAc to give 5.7 g of compound XLV.HCl. A portion of this material (0.50 g) was recrystallized from 95% EtOH for analytical purposes. The NMR and mass spectra were compatible with the indicated structure, and elemental analyses for C, H, and N were all within 0.15% of the theoretical values.

Preparation of 5-((2-Dibenzylamine-1-oxo)ethyl)-2methylbenzenesulfonamide Hydrochloride (XLV.HCl)

Compound XLVI (62.3 g) and two equivalents of dibenzylamine (Aldrich Chemical Co., Milwaukee, Wis. 53233) (84.1 g) were combined in acetone and stirred 4 hours at ambient temperature resulting In precipitation of dibenzylamine hydrobromide, which was removed by filtration. The filtrate was evaporated to dryness and the residue was dissolved in 400 mL isopropanol to which 20.0 mL concentrated HCl was added. The solid which formed was recovered by filtration to give 89.6 g of compound XLV HCl, m.p.=209°–210° C. (dec)

whose NMR was consistent with the proposed structure. The compound was taken for use without further purification.

D. Preparation of 5-((2-Bromo-1-oxo)ethyl)-2-methylbenzenesulfonamide (XLVI)

5-Acetyl-2-methylenzenesulfonamide (Takashi, F. et al., Chem. Pharm. Bull, 30(11), 4092–4101 (1982)) (71.1 g) was suspended in MeOH (900 mL) and stirred at ambient temperature. Bromine (53.4 g) was added over a period of two hours such that the temperature of the reaction mixture did not exceed 25° C. The reaction mixture was evaporated to dryness and the residue was recrytalized from isopropanol (500 mL) to give 62.3 g of compound XLVI, m.p.=142°–143° C. whose NMR was consistent with the structure indicated.

Example 2. Preparation of 5-(1-Hydroxy-2-(((1,2,3,4-tetrahydro-6-methoxy-1-oxo-2-naphthyl)methyl)amino)ethyl)-2-methylbenzene sulfonamide Hydrochloride (XVI.HCl)

Compound XLVII (6.3 g), compound XLIV (4.5 g) and triethylamine (2.7 mL) were combined in acetonitrile (50 mL) and stirred at ambient temperature for 4.5 hours. The reaction mixture was evaporated to dryness and the residue was dissolved in EtOAc which was washed with saturated NaHCO3 solution and distilled H2O, dried with MgSO4, and evaporated to dryness. The residue was twice triturated with boiling isopropanol to give 1.63 g of product as the free base, m.p.=158°–159° C. (dec), whose NMR, mass spectrum, and elemental analyses were consistent with the proposed structure. The free base (1.25 g) was suspended in cold 1N HCl (5.0 mL) to which was added 5.0 mL concentrated HCl. After stirring at 0° C. for 30 minutes the solid was filtered and recrystallized from 95% EtOH to give 0.86 g of XVI.HCl, m.p.=182°–184° C. (dec) whose NMR, mass spectrum, and elemental analyses were all consistent with the indicated structure.

A. Preparation of N-(1,2,3,4-Tetrahydro-6-methoxy-1-oxo-2-naphthyl)methyl-N,N,N-trimethylammonium Iodide (XLVII)

Paraformaldehyde (24 g), 1-oxo-1,2,3,4-tetrahydro-6-methoxynaphthalene (Aldrich Chemical Co., Milwaukee, Wis. 53233) (40 g), dimethylamine hydrochloride (17.1 g) and concentrated HCl (4.5 mL) were combined in EtOH (150 mL) and heated at reflux for 18 hours. Dilution with acetone (1500 mL) and cooling to 4° C. produced white crystals of the intermediate Mannich base HCl salt (24 g). This was collected by filtration and partitioned between EtOAc and excess aqueous NaHCO3. The EtOAc layer was washed with saturated NaCl solution, dried (MgSO4) and evaporated to give 18 g of the oily free base. This oil was dissolved in acetone (200 mL), the solution was filtered, and methyl iodide (13.2 g) was added. The solution was heated at reflux for 15 minutes, cooled to 0° C., and the resulting suspension was filtered, yielding compound XLVII (28 g), as a white solid, m.p. 176°–177° C., which was used without purification.

Example 3. Preparation of 5-(1-(S)Hydroxy-2-(((1,2,3,4-tetrahydro-1-oxo-2-(R,S)-naphthyl)methyl)amino)ethyl)-2-methylbenzenesulfonamide Hydrochloride (XVII.HCl)

Compound XLIII (3.24 g), compound S-(+)-XLIV (2.50 g) and triethylamine (1.7 mL) were combined in acetonitrile (40 mL) and stirred at ambient temperature for 18 hours. The reaction mixture was evaporated to dryness and the residue was dissolved in EtOAc and washed with saturated NaHCO3 solution, dried with MgSO4, and evaporated to dryness. The resulting residue was dissolved in MeOH/concentrated HCl (30 mL/1 mL) and the solution was concentrated to near dryness. The product was precipitated by addition of EtOAc, and was recrystallized from 95% acetonitrile to give, in two crops, 1.48 g of compound XVII.HCl, m.p.=185°–187° C. (dec), $[\alpha]^{20}_D = +38.7°$ (c=1.1, MeOH), whose NMR, mass spectrum, and elemental analyses were consistent with the proposed structure. HPLC analysis of the compound indicated approximately equal amounts of both diastereoisomers.

A. Preparation of S-(+)-5-((1-Hydroxy-2-amino)ethyl)-2-methylbenzenesulfonamide Hydrochloride (S-(+)-XLIV.HCl)

S-(+)-5-(2-Dibenzylamino-1-hydroxyethyl)-2-methylbenzenesulfonamide (XLVIII) (16.2 g), concentrated HCl (3.3 mL) and 20% Pd on C catalyst (0.75 g) were combined in 200 mL 90% EtOH and heated at 33° C. for 24 hours in a Parr hydrogenator under an average hydrogen pressure of 3 atmospheres. The catalyst was filtered off, fresh catalyst (0.60 g) was added, and the mixture was further heated to 33° C. in a Parr hydrogenator under an average hydrogen pressure of 3 atmospheres for 24 hours. The catalyst was filtered once more and the filtrate was evaporated to dryness. The residue was recrystallized from MeOH/EtOAc to give S-(+)-XLIV.HCl, (6.6 g), a white solid, m.p.=187°–190° C. (dec), $[\alpha]^{20}_D = +47.4°$ (c=1.3, MeOH). The NMR, mass spectrum, and elemental analysis were all consistent with the expected structure. The absolute configuration is unknown but is assumed to be S based on analogy with similar compounds.

B. Preparation of R-(−)-5-((1-Hydroxy-2-amino)ethyl)-2-methylbenzenesulfonamide Hydrochloride (R-(−)XLIV.HCl)

This compound was prepared by the method shown above for its enantiomer, S-(+)-XLIV.HCl. Thus, hydrogenolysis of R-(−)-XLVIII (11.3 g) produced 4.82 g R-(−)-XLIV, m.p.=187°–189° C. (dec), $[\alpha]^{20}_D = -47.8°$(c=1.2, MeOH), whose NMR, mass spectrum, and elemental analyses were consistent with the proposed structure. The absolute configuration is unknown, but is assumed to be R based on analogy with similar compounds.

C. Preparation of S-(+)-5-(2-Dibenzylamino-1-hydroxyethyl)-2-methylbenzene-sulfonamide (S-(+)-XLVIII)

Compound XLV (41.4 g) and (+)-β-chlorodiisopinocamphenyl borane (Aldrich Chemical Co., Milwaukee, Wis. 53233) (35.6 g) were combined in dry tetrahydrofuran (100 mL) under N2 at −250° C. The mixture was stirred at −25° C. for 6 hours and then allowed to slowly warm to 5° C. over 18 hours. The solvent was evaporated and the residue was combined with ethyl ether (500 mL) and diethanolamine (37.8 g) and stirred at ambient temperature for 2 hours. The mixture was filtered and the filtrate was evaporated to dryness. The residue was purified by chromatography on a silica gel column, eluting with EtOAc/hexane (1:3), to give 16.2 g of the product as an orange oil.

The NMR of this material was consistent with the expected structure. The compound was taken for hydrogenolysis without further purification. Absolute stereochemistry is unknown but is assumed to be S based on analogy with similar compounds.

D. Preparation of R-(−)-S-(2-Dibenzylamino1-hydroxyethyl)-2-methylbenzene-sulfonamide (R-(−)-XLVIII)

This compound was prepared by the method described above for its enantiomer, (S-(+)-XLVIII). Thus when compound XLV (41.1 g) was reduced with (−)-β-chlorodiisopinocamphenyl borane (Aldrich Chemical Co., Milwaukee, Wis. 53233) (35.6 g), the product, after chromatography on a silica gel column and eluting with EtOAc/hexane (1:3), was compound R-(−)-XLVIII (11.3 g), an orange oil whose NMR was consistent with the proposed structure. The compound was taken for hydrogenolysis without further purification. The absolute configuration is unknown, but is assumed to be R based on analogy with similar compounds.

Example 4. Preparation of 5-(1-(R)-Hydroxy-2-(((1,2,3,4-tetrahydro-1-oxo-2-(R,S)-naphthyl)methyl)amino)ethyl)-2-methylbenzenesulfonamide Hydrochloride (XVIII.HCl)

Compound XLIII (4.53 g), compound R-(−)-XLIV (3.50 g) and triethylamine (2.4 mL) were combined in acetonitrile (50 mL) and stirred at ambient temperature for 18 hours. The reaction mixture was evaporated to dryness and the residue was dissolved in EtOAc and washed with saturated NaHCO₃ solution and then acidified with 1.1 mL concentrated HCl in 10 mL MeOH. The resulting solution was evaporated to dryness leaving a hygroscopic yellow solid which was twice recrystallized from 95% acetonitrile to give 1.60g of compound XVIII.HCl m.p.=189°–190° C. (dec), [α]$^{20}$$_D$=−36.7°(c=1.1, MeOH) whose elemental analysis, mass spectrum, and NMR were consistent with the proposed structure. HPLC analysis of the compound indicated approximately equal amounts of the two possible diastereoisomers.

Example 5. Preparation of 5-(1-(S)-Hydroxy-2-(((1,2,3,4-tetrahydro-6-methoxy-1-oxo-2-(R,S)-naphthyl)methylamino)ethyl)-2-methyl-benzene-sulfonamide Hydrochloride (XIX.HCl)

Compound XLVII (7.50 g), compound S-(+)-XLIV (5.33 g) and triethylamine (3.7 mL) were combined in acetonitrile (80 mL) and stirred at ambient temperature for 3 hours, then stored at −4° C. for 14 hours. Unreacted S-(+)-XLIV was removed by filtration and the filtrate was evaporated to dryness. The resulting residue was dissolved in EtOAc and washed with saturated NaHCO₃ solution, dried with MgSO₄, and evaporated to dryness. The oil remaining was acidified with 2.0 mL concentrated HCl in 10 mL methanol and was partially purified by chromatogrpahy on silica gel with 10% methanol in methylene chloride as eluent. The material thus obtained was acidified with 1.5 mL concentrated HCl in 5 mL methanol and the solution was evaporated to dryness. The resulting solid was recrystallized from acetone/H₂O (95:5) to give 2.4 g of compound (XIX.HCl), m.p.=179°–181° C. (dec), [α]$^{*}$$_D$=+37.5°(c=1.0, MeOH), whose elemental analyses, mass spectrum and NMR were entirely consistent with the structure. HPLC analysis indicated the compound was of >99% overall purity, and was composed of nearly equal amounts of the two possible diastereoisomers.

Example 6. Preparation of 5-91-(R)-Hydroxy-2-(((1,2,3,4-tetrahydro-6-methoxy-1-oxo-2-(R,S)-naphthyl)methyl)amino)ethyl)-2-methylbenzenesulfonamide Hydrochloride (XX.HCl)

Compound XLVII (6.9 g), compound R-(−)-XLIV (4.9 g) and triethylamine (2.5 mL) were combined in 75 mL acetonitrile and stirred at ambient temperature for 20 hours. Unreacted starting materials were removed by filtration, and the filtrate was evaporated to dryness. The residue was dissolved in ethyl acetate and the solution was washed with saturated NaHCO₃ solution, dried (MgSO₄), and then acidified with 1.5 mL concentrated HCl in 10 mL methanol. The acidic solution was evaporated to dryness, and the residue was chromatographed on silica get with 7–10% methanol in methylene chloride as eluent. The oil thus obtained was combined with 1.5 mL concentrated HCl in 10 mL methanol, and the solution was evaporated to dryness leaving a sticky solid which was crystallized by combining with boiling acetone. In this manner, 3.5 g of compound XX.HCl was obtained, m.p.=177°–179° C. (dec), [α]$^{20}$$_D$=−30.6°(c=1.2, MeOH). NMR and mass spectra were compatible with the structure, and the elemental analyses for C. H, and N were within 0.1% of the theoretical values. HPLC analysis indicated the compound contained roughly equal amounts of the two possible diastereoisomers. Example 7. Preparation of 5-(1-Hydroxy-2-(((1,2,3,4-tetrahydro-6,7-dimethoxy-1-oxo-2-naphthyl)methyl)amino)ethyl)-2-methylbenzenesulfonamide Hydrochloride (XXI.HCl)

Compound XLIV.HCl (0.65 g), compound (XLIX) (1.00 g), and triethylamine (0.51 mL) were combined in acetonitrile and stirred at ambient temperature for 3.5 hours. The reaction mixture was evaporated to dryness and the residue was dissolved in ethyl acetate and washed with saturated NaHCO₃ solution. Upon removal of the solvent, an oil was obtained which was chromatographed on silica gel with 10% methanol in CH₂Cl₂ as eluent. The solid free base obtained was converted to the hydrochloride salt by boiling in isopropanol containing one equivalent of concentrated HCl which, after filtration, yielded 0.18 g of compound XXI.HCl, m.p.=191.5°–193° C.(dec). The NMR and mass spectra were consistent with the expected results, and the elemental analyses for C, H, and N were within 0.15% of the theoretical values.

A. Preparation of N-(1,2,3,4-Tetrahydro-6,7-dimethoxy-1-oxo-2-naphthyl)methyl-N,N,N-trimethylammonium Iodide (XLIX)

Paraformaldehyde (4.0 g), 6,7-dimethoxy-1-oxo-1,2,3,4-tetrahydronaphthalene (14.0 g), dimethylamine hydrochloride (5.8 g), and concentrated HCl (1.3 mL) were combined in 70 mL EtOH and heated to reflux for 18 hours. Upon dilution with 350 mL acetone and cooling to 4° C., 14.6 g of solid was obtained which was combined with a similarly obtained 1.3 g of solid and partitioned between EtOAc and saturated aqueous NaHCO₃. The EtOAc solution was dried (MgSO₄) and evaporated to dryness leaving 11.0 g of an oil. This oil was dissolved in 150 mL acetone and to it 4.0 g of methyl iodide was added which resulted in precipitation of a white solid. The white solid was filtered to give 11.7 g of compound XLIX, m.p.=203°-204° C. (dec), whose NMR was consistent with the expected structure. This material was used without further purification.

Example 8. Preparation of 1,2,3,4-Tetrahydro-2-(((2-hydroxy-2-(3-hydroxyphenyl)-ethyl)amino)methyl)-1-naphthalenone (XXII).

Compound XLIII (5.0 g), 2-amino-1-(3-hydroxy)-phenylethanol hydrochloride (Aldrich Chemical Co., Milwaukee, Wis. 53233) (2.8 g), and triethylamine (25 mL) were combined in 100 mL of acetonitrile. The mixture was stirred under $N_2$ at ambient temperature for 18 hours during which time all solids dissolved. An aliquot (25 mL) of the reaction solution was evaporated to dryness leaving a foamy residue which was triturated with hot EtOAc to produce a solid. The crude product was recrystallized from EtOH yielding 0.4 g of compound XXII, m.p.=140°-143° C. Elemental analyses for C, H, and N were within 0.1% of the values calculated for the free base, and the NMR and mass spectra were consistent with the structure.

Example 9. Preparation of 1,2,3,-Tetrahydro-2-(((2-hydroxy-2-(4-hydroxyphenyl)-ethyl)amino)methyl)-1-naphthalenone (XXIII)

Compound XLIII (10.0 g), 2-amino-1-(4-hydroxy)-phenylethanol hydrochloride (Aldrich Chemical Co., Milwaukee, Wis. 53233) (5.5 g), and methylamine (50 mL) were combined in 200 mL acetonitrile and stirred at ambient temperature for 18 hours, which resulted in precipitation of a solid. The solid was filtered and rinsed with acetonitrile to give 8.5 g of compound (XXIII), which was recrystallized from 150 mL EtOH to give 5.5 g of material with m.p.=150°-153° C. (dec), and whose NMR and mass spectra were entirely compatible with the structure. Elemental analyses for C, H, and N were all within 0.1% of the calculated values.

Example 10. Preparation of Methyl 2-hydroxy-5-(1-hydroxy-2-(((1,2,3,4-tetrahydro-1-oxo-2naphthyl)methyl)amino)ethyl)benzoate(XXIV)

Compound XLIII (0.70 g) and methyl 2-hydroxy-5-(1-hydroxy-2-amino)ethyl benzoate.HCl (0.45 g), which may be prepared according to the method of Lederic, et al., J. Med. Chem. 23(7), 738-744, 1980, were combined in 20 mL of N,N-dimethylformamide and stirred for 18 hours at ambient temperature. The solvent was removed and the residue was chromatographed on silica gel with 20:1 $CH_2Cl_2$/MeOH as eluent. The partially purified material thus obtained was recrystallized from methyl ethyl ketone to give 0.09 g of analytically pure product with m.p.=129°-130° C. and whose elemental analyses for C, H, and N were all within 0.1% of the values calculated for the free base. The NMR and mass spectra were consistent with the structure.

Example 11. Preparation of 2-(((2-(4-Chlorophenyl)-2-hydroxyethyl)amino)methyl)-3,4-dihydro-1-(2H)-naphthalenone Hydrochloride(XXV.HCl)

Compound XLIII (3.5 g), compound LI.HCl (2.1 g), and triethylamine (1.4 mL) were combined in 40 mL acetonitrile and stirred at ambient temperature for 4 hours at which time the reaction mixture was evaporated to dryness. The residual material was dissolved in hot EtOAc and washed with 1N NaOH solution. The EtOAc solution was evaporated to dryness leaving a solid which was dissolved in hot methanolic HCl. Addition of excess EtOAc resulted in precipitation of a white solid which was recrystallized from 95% EtOH to yield 1.8 g of compound XXV as the hydrochloride salt, m.p.=181°-183° C. (dec). NMR and mass spectra as well as elemental analyses for C, H, and N were all consistent with the structure.

A. Preparation of 2-Amino-1-(4-chlorphenyl)ethanol Hydrochloride (LI.HCl)

4-Chlorobenzaldehyde (Aldrich Chemical Co., Milwaukee, Wis. 53233) (35.0 g) was dissolved in 100 mL $Et_2O$ and added to 400 mL of a saturated aqueous $NaHSO_3$ solution, which resulted in the formation and precipitation of the bisulfite adduct of 4-chlorobenzaldehyde. The solid bisulfite adduct was added to KCN (24.3 g) in 100 mL $H_2O$ at 0-5° C. Upon stirring and warming to ambient temperature, a yellow oil separated from the aqueous mixture, which was dissolved in 100 mL $Et_2O$ and washed with 200 mL of ice-cold $H_2O$, dried ($MgSO_4$), and evaporated to dryness leaving 40.2 g of the cyanohydrin of 4-chlorobenzaldehyde, which was used without further purification or characterization. The cyanohydrin was dissolved in 200 mL tetrahydrofuran (THF) and added dropwise to a suspension of 28.4 g of lithium tetrahydroaluminate (LAH) in 500 mL THF. After stirring for 2.5 hours at reflux, excess LAH was destroyed by the dropwise addition of 28 mL distilled $H_2O$. 28 mL 15% aqueous NaOH, then 84 mL distilled $H_2O$. The solids were removed by filtration, and the filtrate was evaporated to dryness leaving an oil which was dissolved in aqueous 1N HCl and washed with EtOAc. The pH of the aqueous solution was adjusted to 9-10 with aqueous NaOH solution, and the aqueous solution was extracted with EtOAc. The EtOAc solution was dried ($MgSO_4$), and evaporated to dryness leaving a residue which was dissolved in methanolic HCl. Addition of excess EtOAc to the above solution resulted in precipitation of compound LI.HCl (16.4 g), m.p.=230° C. (dec), whose NMR was entirely consistent with the expected structure.

Example 12. Preparation of 2'-Chloro-5'-(1-Hydroxy-2-(((1,2,3,4-tetrahydro-1-oxo-2-naphthyl)methyl)amino)ethyl)methanesulfonanilide Hydrochloride (XXVI.HCl)

Compound XLIII (6.7 g), compound LII.HCl (5.8 g), and triethylamine (2.7 mL) were dissolved in 75 mL acetonitrile and stirred at ambient temperature for 2 hours. The reaction mixture was acidified with 4.8 mL conc. HCl and evaporated to dryness. The residue which resulted was partitioned between EtOAc and saturated aqueous $NaHCO_3$ solution. The EtOAc solution was dried ($MgSO_4$), and to it was added 1.6 mL concentrated HCl which resulted in the formation of a white solid. After recrystallization from 95% EtOH, 2.4 g of compound XXVI.HCl was obtained, m.p.=177°-179° C. (dec), whose NMR and mass spectra were consistent with the structure and whose elemental analyses for C, H, N, and Cl were all within 0.1% of theory. HPLC analysis showed the compound to be composed of a 9:1 mixture of the two pairs of diastereoisomers.

A. Preparation of 2'-Chloro-5'-((1-hydroxy-2-amino)ethyl)methanesulfonanilide Hydrochloride (LII.HCl)

Compound LIII.HCl (20.1 g) was suspended in 400 mL EtOH and to it NaBH₄ (7.9 g) was added in four portions over 1 hour. The reaction mixture was stirred at ambient temperature for 3 hours and the reaction was quenched by the addition of 52 mL concentrated HCl. EtOH was removed by evaporation and the residue was boiled for 30 minutes with 350 mL MeOH, then with repeated additions of EtOAc, which resulted in precipitation of inorganic salts. The supernatant liquid was separated and evaporated to near dryness. Trituration of the residue with EtOAc produced 11.7 g of a white solid, which was recrystallized from MeOH/EtOAc to give 9.6 g of compound LII.HCl, mp=138°–140° C. (dec), whose NMR and mass spectra were compatible with the indicated structure. The elemental analyses for C, H, and N were within 0.1% of theory for the HCl salt of compound (LII.HCl) containing roughly one-third of a mole of H₂O per mole of compound.

B. Preparation of 2'-Chloro-5'-(1-oxo-2-amino)ethyl)-methanesulfonanilide Hydrochloride (LIII.HCl)

Compound LIV (41.0 g) and 56 mL conc. HCl were dissolved in 800 mL hot EtOH and the solution was refluxed for 2 hours, during which time a precipitate formed. The solid was filtered and recrystallized from 75% EtOH to give 20.1 g of compound LIII.HCl whose NMR was compatible with the expected structure. This material was used without further purification or characterization.

C. Preparation of 2'-Chloro-5'-(1-oxo-2-hexamethylenetetraamino)-methanesulfonanilide Bromide (LIV)

Compound LV (28.0 g) and hexamethylenetetraamine (12.0 g) were combined in 800 mL CH₂Cl₂ and stirred at ambient temperature for 18 hours. The solid which precipitated was recovered by filtration to give a nearly quantitative yield of compound LIV, m.p.=79°–82° C. (dec), whose NMR was generally consistent with the proposed structure.

D. Preparation of 2'-chloro-5'-(1-oxo-2-bromo)ethyl-methanesulfonanilide (LV)

Compound LVI (29.7 g) was suspended in 250 mL MeOH to which was added 19.2 g Br₂ at a rate such that the temperature did not exceed 35° C. The solution which resulted was stirred for an additional 3.5 hours and was then evaporated to dryness. The residue was recrystallized from isopropanol to give 28.0 g of the desired product, m.p.=124°–125° C., which was deemed of adequate purity for synthetic use on the basis of NMR and TLC.

E. Preparation of 2-chloro-5-acetylmethanesulfonanilide (LVI)

To an ice chilled solution of compound LVII.HCl (32.8 g) and pyridine (34.3 mL) in 350 mL acetonitrile was dropwise added methanesulfonyl chloride (18.8 mL). After warming to ambient temperature while stirring over 18 hours, the reaction mixture was poured into 3 L ice water which was acidifed with concentrated HCl to pH=1–2. The solids were recovered by filtration to give 29.8 g of compound LVI, m.p.=112°–115° C. The NMR spectrum was consistent with the structure.

F. Preparation of 3-Amino-4-chloroacetophenone Hydrochloride (LVII.HCl)

4-Chloro-3-nitroacetophenone (Aldrich Chemical Co., Milwaukee, Wis. 53233) (41.5 g) was combined with iron metal filings (55.9 g) and concentrated HCl (4.0 mL) in 400 mL 75% ethanol. After refluxing for 3 hours, the reaction mixture was stirred at ambient temperature for 18 hours at which point additional iron metal filings (55.9 g) were added and reflux was resumed for 1 hour. The reaction mixture was filtered and to the filtrate concentrated HCl (18.0 mL) was added. Concentration of the acidic solution resulted in precipitation of a solid, which was recrystallized from aqueous methanol and ethyl acetate to yield 32.8 g of compound LVII.HCl, m.p.=189°–192° C. (dec), whose NMR spectrum was compatible with the structure. The material was used for synthesis without further purification or characterization.

Example 13. Preparation of 2-(((2-(4-Chlorophenyl)-2-hydroxyethyl)-amino)methyl)-3,4-dihydro-6-methoxy-1(2H)-naphthalenone Hydrochloride (XXVII.HCl)

Compound XLVII (3.8 g), compound LI.HCl (2.1 g), and triethylamine (1.4 mL) were combined in 40 mL acetonitrile and stirred under N₂ at ambient temperature for 3 hours. The reaction mixture was filtered, and the solids were suspended in aqueous base (pH=9–10). The solids were recovered by filtration from the basic suspension and rinsed with H₂O to give 1.6 g of free base, which was converted to the HCl salt by dissolving in 80 mL hot MeOH and adding to it 0.5 mL concentrated HCl. Dilution of the resulting suspension with EtOAc resulted in recovery of 1.5 g of compound XXVII.HCl, a white solid, m.p.=195°–197° C. (dec), whose NMR and mass spectra were consistent with the structure. Elemental analyses for C, H, N, and Cl were all within 0.1% of the theoretical values.

Example 14. Preparation of 2'-Chloro-5'-(1-hydroxy-2-(((1,2,3,4-tetrahydro-7-chloro-1-oxo-2-naphthyl)methyl)amino)ethyl)-methanesulfonanilide Hydrochloride (XXVIII.HCl)

Compound LVIII (0.8 g), compound LII.HCl (0.6 g), and triethylamine (0.3 mL) were stirred in 7 mL acetonitrile at ambient temperature for 2.5 hours. The reaction solution was evaporated to dryness and the residue was dissolved in ethyl acetate and washed with saturated aqueous NaHCO₃ solution. After drying the organic solution with MgSO₄ and evaporating the solvent, 0.7 g of a foam was obtained which was combined with 0.2 mL conc. HCl in 10 mL MeOH. Removal of the solvent produced 0.8 g of crude product as the HCl salt, which was purified by flash chromatography on silica gel eluting with 3% methanol in CH₂Cl₂. Fractions containing the pure product were combined and acidified with 0.2 mL concentrated HCl in 1 mL MeOH. Removal of the solvent resulted in 0.2g of white foam, XXVIII.HCl. No melting point was recorded as the product contained water which it began to lose on heating from 92° C. NMR and mass spectra were consistent with the expected structure, while elemental analyses for C, H, N, and Cl were all within 0.1% of the values calculated for the HCl salt containing 0.5 mole H₂O.

A. Preparation of N-(7-Chloro-1,2,3,4-tetrahydro-1-oxo-2-naphthyl)methyl-N,N,N-trimethyl ammonium Iodide (LVIII)

7-Chloro-1-tetralone (obtained by the method of Fieser and Seligman, J. Am. Chem. Soc. 60 170

(1938) for the preparation of 7-bromo-1-tetralone) (9.0 g), paraformaldehyde (3.1 g), dimethylamine hydrochloride (4.3 g) and concentrated HCl (0.8 mL) were refluxed in 40 mL EtOH under N₂ for 18 hours. Dilution of the reaction mixture at this time with 500 mL acetone resulted in precipitation of a white solid which was recovered by filtration. The solid was partitioned between saturated aqueous NaHCO₃ solution and ethyl acetate. The ethyl acetate solution was dried (MgSO₄) and evaporated to dryness. The resulting residue was combined with CH₃I (4.8 g) in 100 mL ethyl acetate producing in two crops 11.5 g of compound LVIII, m.p.=192°-193.5° C. (dec). The NMR spectrum was compatible with the indicated structure.

Example 15. Preparation of 4'-(2-(((7-chloro-1,2,3,4-tetrahydro-1-oxo-2-naphthyl)-methyl)amino)-1-hydroxyethyl)methanesulfonanilide Hydrochloride (XXIX.HCl)

2-Amino-1-hydroxyethylmethanesulfonanilide hydrochloride (European Patent Application 338,793), compound LIX.HCl (1.3 g), compound LVIII (1.9 g), and triethylamine (0.7 mL) were combined in 25 mL acetonitrile and stirred at ambient temperature under N₂ for 3 hours, at which point the reaction mixture was filtered and the solids dissolved in hot methanolic HCl. Dilution of this solution with EtOAc resulted in precipitation of a white solid, which was once more precipitated from aqueous MeOH by the addition of EtOAc to give 1.1 g of white solid, m.p.=179°-182° C. (dec). The NMR and mass spectra were consistent with the indicated structure, and the elemental analyses for C, H, and N were all within 0.1% of the theoretical values.

Example 16. Preparation of 2-(((2-(3,4-Dichlorophenyl)-2-hydroxyethyl)amino)methyl)-3,4-dihydro-1(2H)-naphthalenone Hydrochloride (XXX.HCl)

Compound XLIII (1.42 g) 1-(3,4-dichlorophenyl)-2-aminoethanolhydrochloride (1.0 g) (Glynn and Linnell, Quart, J. Pharmacol. 5, 480–492 (1932)) and triethylamine (0.6 mL) were combined in 15 mL acetonitrile and stirred at ambient temperature for 2 hours, at which point the reaction mixture was filtered. The filter cake was dissolved in boiling methanolic HCl and the solution was diluted with EtOAc which resulted in precipitation of a white solid. The crude product was recrystallized from 95% EtOH to give 0.5 g of compound XXX as the hydrochloride salt, m.p.=186°-187° C. (dec), whose NMR and mass spectra were consistent with the indicated structure and whose elemental analyses for C, H, N, and Cl were within 0.05% of the calculated values for the indicated compound containing one-fourth mole of H₂O.

Example 17. Preparation of 2-Hydroxy-5-(1-hydroxy-2-(((1,2,3,4-tetrahydro-1-oxo-2-naphthyl)methyl)amino)ethyl)benzamide Hydrochloride (XXXI.HCl)

Two reactions consisting of combining compound XLIII (5.2 g), and compound LX.HCl 5-(2-amino-1-hydroxyethyl)salicylamide hydrochloride (U.S. Pat. No. 4,379,166) (4.2 g) with triethylamine (2.8 mL) in 40 mL acetonitrile were carried out simultaneously. After stirring under N₂ at ambient temperature for 24 hours the two reaction mixtures were combined and the volatiles were removed by evaporation. The residue was dissolved in EtOAc and washed with a saturated aqueous NaHCO₃ solution. The EtOAc solution was dried (MgSO₄) and evaporated to dryness. The residue was dissolved in 60 mL hot EtOH to which was added 2.0 mL concentrated HCl. The EtOH was removed by evaporation and was replaced by a mixture of MeOH and EtOAc which resulted in precipitation of a tan solid. This material was recrystallized from a mixture of EtOH/H₂O/EtOAc to give 0.8 g of compound XXXI.HCl, m.p.=201° C. (dec), whose NMR and mass spectra were consistent with the indicated structure. Elemental analyses for C, H, and N were all within 0.05% of the values calculated.

Example 18. Preparation of 2-Hydroxy-5-(1-hydroxy-2-(((1,2,3,4-tetrahydro-6-methoxy-1-oxo-2-naphthyl)methyl)amino)ethyl)benzamide Hydrochloride (XXXII.HCl)

5-(2-Amino-1-hydroxyethyl)salicylamide (U.S. Pat. No. 4,379,166), compound XLVII (3.5 g), compound LX.HCl (2.4 g), and triethylamine (1.4 mL) were combined in 15 mL pyridine and stirred at ambient temperature for 24 hours, at which point the reaction mixture was diluted with 50 mL EtOAc and then filtered to remove solids. The filtrate was concentrated and triturated with EtOAc, producing a solid material which was suspended in an aqueous Na₂CO₃ solution (pH>8) and stirred at. ambient temperature for 18 hours. The solid was recovered, dissolved in hot methanolic HCl, and the product was precipitated as the HCl salt by addition of EtOAc, yielding compound XXXII.HCl (0.5 g), m.p.=148°-151° C. (dec). The NMR and mass spectra were compatible with the structure indicated, and the elemental analyses for C, H, and N were all within 0.05% of the theoretical values.

Example 19. Preparation of 4-(2-(((1,2,3,4-Tetrahydro-1-oxo-2-naphthyl)methyl)amino)ethyl)benzenesulfonamide-HCl (XXXIII.HCl)

Compound XLIII (8.0 g), 4-(2-aminoethyl)benzenesulfonamide (Aldrich Chemical Co., Milwaukee, Wis. 53233) (2.2 g), and triethylamine (3.0 mL) were combined in 50 mL acetonitrile and stirred at ambient temperature for 18 hours, at which time solids were filtered and rinsed with acetonitrile to give 7.6 g of white solid. This material was combined with 2.2 g of solid obtained similarly (from 4.0 g compound XLIII, 2.3 g 4-(2-aminoethyl)benzenesulfonamide, and 1.5 mL triethylamine) in 200 mL MeOH and 1.9 mL concentrated HCl. The suspension was heated to boiling for 20 minutes and then cooled to ambient temperature at which point the solid was recovered by filtration to give compound XXXIII.HCl (6.9 g), m.p.=207°-208° C., whose NMR and mass spectra were entirely compatible with the structure, and whose elemental analyses for C, H, N, and S were all within 0.2% of the theoretical values.

Example 20. Preparation of 4'-(1-Hydroxy-2-(((1,2,3,4-tetrahydro-1-oxo-2-naphthyl)-methyl)amino)ethyl)ethanesulfonanilide (XXXIV)

Compound XLIII (3.4 g), compound LXI.HCl (2.8 g), and triethylamine (1.9 mL) were combined in 25 mL acetonitrile and stirred at ambient temperature under N₂ for 15 minutes, then at 0° C. for 1.5 hours. At this point the reaction mixture was evaporated to dryness, and the residue was dissolved in EtOAc and washed with aqueous NH4OH. The organic solution was dried (MgSO4) and evaporated to dryness leaving an oil which was crystallized from isopropanol to yield 0.1 g of compound XXXIV, m.p.=120.5°–122° C., whose NMR and mass spectra were consistent with the structure. Elemental analyses for C, H, and N suggested the compound contained 0.2 equivalents of $H_2O$ and a trace of isopropanol.

A. Preparation of 4'-((2-Amino-1-hydroxy)ethyl)ethanesulfonanilide Hydrochloride (LXI.HCl)

4'-((2-Dibenzylamino-1-oxo)ethyl)ethanesulfonanilide LXII (12.7 g) and concentrated HCl (2.6 mL) were combined in MeOH (150 mL) with 0.35 g of 20% Pd/C catalyst and shaken under 3 atmospheres of hydrogen at 30°–35° C. After 6 hr fresh catalyst was added and the shaking was continued as before for 72 hours. The catalyst was filtered and the filtrate was evaporated to dryness leaving an oily residue which was purified by flash chromatography on silica gel eluting with 5:95:1 methanol/$CH_2Cl_2$/NH4OH. The product thus obtained was converted to the HCl salt by stirring in isopropanol containing excess hydrochloric acid. After evaporating the isopropanol and drying under high vacuum, 5.3 g of a foamy solid was obtained whose NMR was consistent with the indicated structure. The compound was used without further purification.

B. Preparation of 4'-((2-Dibenzylamino-1-oxo)ethyl)ethanesulfonanilide (LXII)

Compound LXIII (21.0 g) was dissolved in 300 mL acetone, and to it dibenzylamine (27.6 g) was added. After 2.5 hours, the solid dibenzylamine hydrobromide was filtered off, and the filtrate was evaporated to dryness. The residue was dissolved in EtOAc and washed with aqueous NH40H, dried (MgSO4), and evaporated to dryness leaving an oil which was crystallized from EtOH to give 16.3 g compound LXII, m.p.=102°–103.5° C., whose NMR was compatible with the structure.

C. Preparation of 4'-((2-Bromo-1-oxo)ethyl)ethanesulfonanilide (LXIII)

To a suspension of compound LXIV (30.0 g) in 400 mL methanol was added $Br_2$ (20.8 g) in 100 mL MeOH. The resulting solution was stirred at ambient temperature for 18 hours and was then concentrated in vacuo until precipitation of a solid occurred. The solid was filtered, and the filtrate was concentrated in vacuo once again to yield a second crop of crystalline solid, which was filtered. The two batches of solid were combined and recrystallized from ethyl acetate to give 22.5 g of compound LXIII, m.p.=149°–152° C., whose NMR was consistent with the structure. The material was used without further purification.

D. Preparation of 4-Acetylethanesulfonanilide (LXIV)

4-Amino-acetophenone (Aldrich Chemical Co., Milwaukee, Wis. 53233) (50.0 g) and pyridine (33.0 mL) were combined in 200 mL acetonitrile at 0° C. Ethanesulfonyl chloride (Aldrich Chemical Co., Milwaukee, Wis. 53233) (36.9 mL) was added dropwise at 0° C. and the solution was allowed to come to ambient temperature and stirred for 18 hours. The solution was then poured into 2.0L ice/$H_2O$ and the resulting solid was filtered to give 80.3 g of 4-acetylethanesulfonanilide, m.p=131°–133° C., whose NMR was compatible with the expected structure. The material was used without further purification.

Example 21. Preparation of 4'-(1-Hydroxy-2-(((1,2,3,4-tetrahydro-1-oxo-2-naphthyl)-methyl)amino)ethyl)-N-methylmethanesulfonanilide Hydrochloride (XXXV HCl)

Compound XLIII (5.2 g), compound LXV (4.2 g), and triethylamine (2.8 mL) were stirred in 60 mL acetonitrile at ambient temperature for 20 hours. At this time the solids were recovered by filtration and dissolved in hot methanolic HCl. The product was precipitated as the HCl salt by addition of excess ethyl acetate to give (XXXV.HCl) (4.2 g), m.p.=187°–189° C. (dec), for which the NMR and mass spectra were compatible. Elemental analyses for C, H, and N were within 0.15% of the calculated values.

A. Preparation of 4-(1-Hydroxy-2-amino)ethyl-N-methylmethanesulfonanilide Hydrochloride (LXV.HCl)

Compound LXVI (7.0 g) and 20% Pd/C (0.5 g) were combined in 150 mL MeOH and shaken under 3 atmospheres of $H_2$ gas at 25°–30° C. for 20 hours. The catalyst was filtered off and the filtrate was acidified with concentrated HCl (1.5 mL). The product was precipitated from the methanolic HCl solution by addition of excess ethyl acetate to give compound LXV.HCl (3.9 g), m.p.=205°–208° C. (dec), whose NMR spectrum was consistent with the expected structure.

B. Preparation of 4-(2-Dibenzylamino-1-oxo)ethyl-N-methylmethanesulfonanilide (LXVI)

4'-(2-Dibenzylamino-1-oxo)ethylmethanesulfonanilide (European Patent Application 338,793), compound LXVII, (20.0 g) was dissolved in 250 mL acetone and heated at reflux. Methyl p-toluenesulfonate (Aldrich Chemical Co., Milwaukee, Wis. 53233) (45.6 g) as a 100 mL solution in acetone was added in several portions alternately with 50 mL of 30% aqueous NaOH solution. After 45 minutes, the reaction mixture was evaporated to dryness, and the residue was dissolved in ethyl acetate and washed with aqueous NaOH, then $H_2O$, dried (MgSO4) and evaporated to dryness. The crude material thus obtained was chromatographed on silica gel with 2% MeOH/$CH_2Cl_2$ as eluent to give 15.6 g of a yellow solid, which was combined with 0.8 g of similarly obtained material and recrystallized from ethyl acetate and hexanes to give compound LXVI (7.2 g), m.p.=117°–120° C. (dec), whose NMR was consistent with the structure. The compound was used without further purification.

Example 22. Preparation of 4'-(1-Hydroxy-2-((1,2,3,4-tetrahydro-6-methoxy-1-oxo-2-naphthyl)methyl)amino)ethyl-N-methylmethanesulfonanilide Hydrochloride (XXXVI.HCl)

Compound XLVII (1.3 g), compound LXV.HCl (1.0 g), and triethylamine (0.5 mL) were combined in 15 mL acetonitrile and stirred under $N_2$ at ambient temperature for 3 hours. The suspended solids were filtered and stirred with NaHCO3 in $H_2O$, then filtered once more, at which point the filtered material was dissolved in methanolic HCl. The acidic solution was evaporated to dryness and the residue was recrystallized from methanol and ethyl acetate to give 0.4 g of compound XXXVI.HCl, m.p.=183°–185° C. (dec). The NMR and mass spectra were consistent with the structure, as were the elemental analyses for C, H, and N.

Example 23. Preparation of 4'-(2-(((1,2,3,4-Tetrahydro-7-bromo-1-oxo-2-naphthyl)methyl)amino)-1-hydroxyethyl)methanesulfonanilide Hydrochloride (XXXVII.HCl)

Compound LIX (0.5 g) and compound LXIX (0.9 g) were stirred in 15 mL acetonitrile at ambient temperature for 3.5 hours. The solid material was recovered by filtration and stirred with aqueous NaHCO₃ for 15 minutes. The solid was filtered, vacuum dried, and dissolved in boiling methanolic HCl. Dilution with ethyl acetate produced a white solid, which upon filtration gave 0.7 g XXXVII.HCl, m.p.=190°-191° C. (dec), whose NMR and mass spectra were consistent with the indicated structure. Elemental analyses for C, H, and N were all within 0.1% of the calculated values.

A. Preparation of N-(7-Bromo-1,2,3,4-tetrahydro-1-oxo-2-naphthyl)methyl-N,N,N-trimethylammonium Iodide (LXIX)

7-Bromo-1,2,3,4-tetrahydronaphthalen-1-one (Fieser and Seligman J. Am. Chem. Soc. 60, 170 (1988)) (3.4 g), paraformaldehyde (0.9 g), dimethylamine hydrochloride (1.3 g), and concentrated HCl (0.2 mL) were refluxed for 6 hours under $N_2$. Upon dilution of the reaction mixture with 100 mL acetone a solid was obtained which was partitioned between ethyl acetate and saturated aqueous NaHCO₃. The ethyl acetate solution was dried (MgSO₄) and evaporated to dryness. The residue was combined with 1.6 g CH₃I in ethyl acetate which produced a white precipitate. Upon filtration 2.7 g of compound LXIX was obtained, m.p.=185°-187° C. (dec). The NMR spectrum was consistent with the structure.

Example 24. Preparation of 4'-(1-Hydroxy-2-(((1,2,3,4-tetrahydro-7-methoxy-1-oxo-2-naphthyl)methyl)amino)ethyl)methanesulfonanilide Hydrochlroide (XXXVIII.HCl)

Compound LIX.HCl (1.0 g), compound LXX (1.4 g), and triethylamine (0.5 mL) were stirred in 15 mL acetonitrile at ambient temperature for 3 hours. The solid material was filtered off and dissolved in boiling methanolic HCl. Addition of EtOAc to this boiling solution resulted in precipitation of a white solid, which was recrystallized from 95% ethanol to give 0.5 g of compound XXXVIII.HCl, m.p.=170°-172° C. (dec), whose NMR and mass spectra were consistent with the indicated structure. The elemental analysis for C, H, and N suggested that approximately 2% of the product was the HI salt rather than the HCl salt.

Preparation of N-(7-Methoxy-1,2,3,4-tetrahydro-1-oxo-2- naphthyl)methyl-N,N,N-trimethylammonium Iodide (LXX)

Paraformaldehyde (8.5 g), dimethylamine hydrochloride (11.6 g), and 7-methoxy-1-oxo-1,2,3,4-tetrahydronaphthalene (Aldrich Chemical Co., Milwaukee, Wis. 53233) (25.0 g) were heated at reflux in 70 mL EtOH with 2.4 mL concentrated HCl for 18 hours. The resulting suspension was diluted with 500 mL acetone and the solids were filtered and partitioned between EtOAc and saturated aqueous NaHCl₃ solution. The ethyl acetate solution was dried (MgSO₄) and evaporated to dryness leaving an oil which was dissolved in 200 mL acetone. Addition of 16.8 g of methyl iodide resulted in formation of a white solid which was recovered by filtration to give compound LXX (27.6 g), m.p.=144°-146° C. (dec). This material was used without further purification.

Example 25. Preparation of 4'-(1-Hydroxy-2-(((1,2,3,4-tetrahydro-6,7-dimethoxy-1-oxo-2-naphthyl)methyl)amino)ethyl)methanesulfonanilide (XXXIX)

Compound XLIX (1.0 g), compound LIX.HCl (0.7 g), and triethylamine (0.5 mL) were combined in 6 mL acetonitrile and stirred at ambient temperature for 2.5 hours. The suspended solids were filtered, dissolved in EtOAc, and washed with aqueous NaHCO₃. The organics were then chromatographed on silica gel eluting with MeOH/CH₂Cl₂/NH₄OH (2:25:.25) to give 0.2 g XXXIX, m.p.=139°-141° C. (dec), whose NMR and mass spectra were compatible with the expected structure. The elemental analyses for C, H, and N were all within 0.45% of the values calculated for the free base.

Example 26. Preparation of 4'-(1-Hydroxy-2-(((1,2,3,4-tetrahydro-7-nitro-1-oxo-2-naphthyl)methyl)amino)ethyl)methanesuflonanilide Hydrochloride (XL.HCl)

Compound (LXXI) (1.0 g) and compound LIX (0.6 g) were combined in 10 mL acetonitrile and stirred at ambient temperature for 2 hours. At this time the solids were recovered by filtration and suspended in aqueous NaHCO₃ for 2 hours. The solid free base was filtered and dried to give 0.7 g white solid. This material was converted to the HCl salt by stirring in 15 mL 1N HCl at ambient temperature, followed by cooling and diluting with 20 mL 6N HCl. Upon filtration 0.6 g of compound XL.HCl was obtained. m.p.=165°-167° C. (dec). The NMR and mass spectra were entirely consistent with the indicated structure, and the elemental analyses for C, H, and N were all within 0.05% of the values calculated for HCl salt containing 0.25 mole H₂O.

A. Preparation of N-(7-Nitro-1,2,3,4-tetrahydro-1-oxo-2-naphthyl)-methyl-N,N,N-trimethylammonium Iodide (LXXI)

7-Nitro-1-tetralone (Lancaster Synthesis Ltd., Windham, N.H. 03087) (5.0 g), paraformaldehyde (1.6 g), dimethylamine hydrochloride (2.3 g), and concentrated HCl (0.4 mL) were refluxed in 15 mL EtOH under N₂ for 6 hours. Upon dilution with 100 mL acetone, a solid was obtained which was filtered off and partitioned between ethyl acetate and saturated aqueous NaHCO₃. The ethyl acetate solution was dried (MgSO₄) and evaporated to dryness leaving 3.6 g of yellow solid. The solid was combined with CH₃I(2.6 g) in 35 mL EtOAc which resulted in formation of a precipitate. Upon filtration 4.7 g of compound LXXI was obtained, m.p.=171°-172° C. (dec). The NMR was consistent with the indicated structure, and the compound was used without further purification.

Example 27. Preparation of 4'-(1-Hydroxy-2-(((1,2,3,4-tetrahydro-6-hydroxy-1-oxo-2-naphthyl)methyl)amino)ethyl)methanesulfonanilide Hydrochloride (XLI-HCl)

Compound LXXII (2.0 g), compound LIX.HCl (1.6 g), and triethylamine (1.1 mL) were stirred at ambient temperature for 18 hours at which point the reaction mixture was filtered. The solid was dissolved in hot methanolic HCl and the solution was diluted with ethyl acetate which produced a white precipitate. This solid was recrystallized from 75% ethanol to give 0.7 g XLI.HCl, m.p.=204°-205° C. (dec), whose NMR and mass spectra were consistent with the structure. The elemental analyses for C, H, and N were within 0.2% of the values calculated.

A. Preparation of N-(6-Hydroxy-1,2,3,4-tetrahydro-1-oxo-2-naphthyl)methyl-N,N,N-trimethylammonium Iodide (LXXII)

Compound XLVII (15.0 g) was suspended in 500 mL $CH_2Cl_2$ at −5°...10° C., and to it was added over 30 minutes 150 mL of a 1M solution of $BBr_3$ in $CH_2Cl_2$ (Aldrich Chemical Co., Milwaukee, Wis. 53233). The reaction mixture was allowed to warm to ambient temperature and then stirred for an additional 45 minutes. Excess $BBr_3$ was destroyed by the cautious addition of 120 mL 6N HCl, and the reaction mixture was evaporated to remove $CH_2Cl_2$. The resulting aqueous suspension was chilled at 4° C. for 18 hours and the solid was filtered to give 15.4 g of crude product. After a recrystallization from 80% EtOH, 8.5 g of compound LXXII, m.p.=202°-205° C. (dec) was obtained. The NMR spectrum was compatible with the structure.

Example 28. Antihypertensive Activity

The blood pressure lowering activities of compounds of formula (I) were evaluated in conscious, genetically hypertensive rats (Charles River Breeding Laboratories, Inc., Wilmington, Mass. 01887). The results of these studies are summarized in Table I for a selected number of compounds.

Spontaneously Hypertensive Rats

Spontaneously hypertensive rats (Charles River), weighing between 300–450 g, were used in this study. Systolic and diastolic blood pressure measurements were made directly from the indwelling arterial cannula.

On the day of surgery, rats were anesthetized with sodium pentobarbital, 50 mg/kg, i.p. The right femoral artery was cannulated with a polyethylene tube (PE50, i.d. 0.023″), filled with 10% heparinized saline, the tip of which was drawn to approximately the size of a PE10 tube (i.d. 0.011 ″). The tip of the cannula was advanced into the aorta just below the level of the kidneys. The opposite end of the cannula was passed under the skin and exteriorized at the back of the neck near the shoulder blades. It was then passed through a metal spring tether and a saddle (BRS/LVE, Beltsville, Md.) which was stitched and taped to the back of the rat. Rats were housed in individual cages and allowed to recover for three days. Patency of the cannula was maintained by withdrawing heparinized saline, flushing with normal saline and then replacing the cannula dead space with 10% heparinized saline (0.3 mL).

Blood pressure was continuously monitored using a Starham pressure transducer (p23id) and recorded on a Grass polygraph (Model 7) and the readings were digitized using a cardiovascular analyzer and a data logger (Buxco Electronics).

On experimental day one, control (baseline) blood pressure readings were obtained for 3 hours and were averaged. The test compound was administered p.o. or i.p. and the blood pressure monitored for the next 24 hours. This was followed by the next dose of the test compound and the procedure was repeated for the next 2–3 days. Blood pressure was continuously monitored and the readings were averaged for each hour after administering the test compound. Changes in systolic and diastolic blood pressures from control (pre-drug) values were expressed in percent.

Compound were dissolved in distilled water (for oral dosing) or normal saline (for i.p. injection). 0.5% Methyl cellulose was used as the vehicle in some cases. The injection volume was 0.1–0.2 ml/100 g body weight.

TABLE I

Blood Pressure Lowering Activity of Selected Compounds in Spontaneously Hypertensive Rats

| Compound (10 mg/kg p.o.) | Example No. | % Decrease in Blood Presure (mm Hg) Systolic/Diastolic |
|---|---|---|
| XV | 1 | 25 ± 4/26 ± 4 |
| XVI | 2 | 24 ± 1/24 ± 2 |
| XVII | 3 | 28 ± 5/29 ± 5 |
| XVIII | 4 | 15 ± 3/14 ± 4 |
| XIX | 5 | 35 ± 8/36 ± 11 |
| XX | 6 | 19 ± 4/21 ± 2 |
| XXI | 7 | 18 ± 3/24 ± 4 (at 30 mg/kg p.o.) |
| XXII | 8 | 26 ± 4/24 ± 5 |
| XXIII | 9 | 22 ± 5/21 ± 4 |
| XXIV | 10 | 16 ± 5/14 ± 6 |
| XXV | 11 | 16 ± 1/20 ± 0 |
| XXVI | 12 | 46 ± 3/53 ± 5 |
| XXVII | 13 | 10 ± 3/11 ± 0 |
| XXIX | 15 | 13 ± 1/18 ± 4 |
| XXX | 16 | 16 ± 0/17 ± 2 |
| XXXI | 17 | 17 ± 2/21 ± 2 |
| XXXII | 18 | 18 ± 2/20 ± 1 |
| XXXIII | 19 | 17 ± 6/18 ± 7 |
| XXXIV | 20 | 19 ± 5/20 ± 2 |
| XXXV | 21 | 29 ± 6/32 ± 6 |
| XXXVI | 22 | 17 ± 3/16 ± 5 |
| XL | 26 | 16 ± 1/18 ± 2 (at 30 mg/kg p.o.) |

Example 29. Formulations

| A-Injection | |
|---|---|
| Ingredient | Amount per Ampule |
| Compound of Formula I | 250.0 mg |
| Sodium Chloride | 8.5 mg |
| Water for Injections, q.s. | 1.0 mL |

The finely ground active compound and sodium chloride are dissolved in the Water for Injections. The solution is filtered and sterilized by autoclaving.

| B-Suppository | |
|---|---|
| Ingredient | Amount per Suppository |
| Compound of Formula I | 250.0 mg |
| Cocoa Butter, q.s. or Wecobee ™ Base | 2.0 g |

Wecobee is the trademark of a hydrogenated carboxylic acid.

The finely ground active compound is mixed with the melted suppository base (either Cocoa Butter or Wecobee ™ Base), poured into molds and allowed to cool to afford the desired suppositories.

| C-Syrup | |
|---|---|
| Ingredient | Amount per 5 mL |
| Compound of Formula I | 250.0 mg |
| Glycerol | 500.0 mg |
| Sucrose | 3500.0 mg |
| Methylparaben | 5.0 mg |
| Cherry Flavoring | 0.005 mL |
| Coloring | q.s. |

| C-Syrup | |
|---|---|
| Ingredient | Amount per 5 mL |
| Water | q.s. to 5.0 mL |

Glycerol, sucrose, methylparaben, and flavoring are combined in 70% of the total batch quantity of water. Coloring and the active compound are dissolved in the remaining water, then the two solutions are mixed and clarified by filtration.

| D-Tablet | |
|---|---|
| Ingredient | Amount per Tablet |
| Compound of Formula I | 250.0 mg |
| Lactose | 125.0 |
| Corn Starch | 50.0 |
| Polyvinylpyrrolidone | 3.0 |
| Stearic acid | 1.0 |
| Magnesium stearate | 1.0 |

The active compound is finely ground and intimately mixed with the powdered excipients lactose, corn starch, polyvinylpyrrolidone, magnesium stearate and stearic acid. The formulation is then compressed to afford a tablet weighing 430 mg.

| E-Capsule | |
|---|---|
| Ingredient | Amount per Capsule |
| Compound of Formula I | 250.0 mg |
| Lactose | 174.0 |
| Corn Starch | 174.0 |
| Stearic acid | 2.0 |

The finely ground active compound is mixed with the powdered excipients lactose, corn starch and stearic acid and packed into gelatin capsules.

We claim:

1. The compound 2'-chloro-5'-(1-hydroxy-2-(((1,2,3,4-tetrahydro-1-oxo-2-naphthyl)methyl)amino)ethyl)-methanesulfonanilide or a pharmaceutically acceptable salt thereof.

2. The hydrochloride, hydroiodide, sulfate, methanesulfonate or toluenesulfonate salt of a compound of claim 1.

3. A method for the treatment of hypertension in a mammal which comprises administering to said mammal a therapeutically effective antihypertensive amount of a compound of claim 1 or a pharmaceutically acceptable salt thereof.

4. A pharmaceutical composition comprising a compound of claim 1 or a pharmaceutically acceptable salt thereof and a pharmaceutically acceptable carrier therefor.

* * * * *